(12) United States Patent
Foker

(10) Patent No.: US 8,710,018 B2
(45) Date of Patent: Apr. 29, 2014

(54) METHODS AND COMPOSITIONS FOR INHIBITING PROGRESSION TO CHRONIC CARDIAC FAILURE

(76) Inventor: John E. Foker, River Falls, WI (US)

( * ) Notice: Subject to any disclaimer, the term of this patent is extended or adjusted under 35 U.S.C. 154(b) by 0 days.

(21) Appl. No.: 12/864,408

(22) PCT Filed: Jan. 23, 2009

(86) PCT No.: PCT/US2009/031910
§ 371 (c)(1),
(2), (4) Date: Oct. 27, 2010

(87) PCT Pub. No.: WO2009/094593
PCT Pub. Date: Jul. 30, 2009

(65) Prior Publication Data
US 2011/0053869 A1 Mar. 3, 2011

Related U.S. Application Data

(60) Provisional application No. 61/023,712, filed on Jan. 25, 2008.

(51) Int. Cl.
*A61K 31/70* (2006.01)

(52) U.S. Cl.
USPC .......................................................... 514/23

(58) Field of Classification Search
USPC .......................................................... 514/23
See application file for complete search history.

(56) References Cited

U.S. PATENT DOCUMENTS

| 3,592,245 | A | * | 7/1971 | Schneller et al. ............... 141/25 |
| 4,605,644 | A |   | 8/1986 | Foker |
| 4,719,201 | A | * | 1/1988 | Foker ............................. 514/23 |
| 6,218,366 | B1 | * | 4/2001 | St. Cyr et al. .................. 514/23 |
| 6,339,716 | B1 |   | 1/2002 | Sawada et al. |
| 6,534,480 | B2 |   | 3/2003 | Cyr et al. |
| 7,553,817 | B2 |   | 6/2009 | Butler et al. |

OTHER PUBLICATIONS

Khoynezhad, A. et al. "A Synopsis of Research in Cardiac Apoptosis and Its Application to Congestive Heart Failure" Tex. Heart Inst. J. 34 (2007) 352-9.
Pauly, DF et al. "D-Ribose as a Supplement for Cardiac Energy Metabolism" J. Cardiovasc. Pharmacol. Therapeut. 5 (4) (2000) 249-258.
Seifart, HI et al. "The influence of various precursors on the concentration of energy-rich phosphates and pyridine nucleotides in cardiac tissue and its possible meaning for anoxic survival" Basic Research in Cardiology. 75(1) (1980) 57-61.
Varnava AM et al. "Restricted weekend service inappropriately delays discharge after acute myocardial infarction" Heart 87 (2002) 216-219.
Zimmer, HG "Normalization of depressed heart function in rats by ribose" Science 220 (4592) (1983) 81-82.
Zimmer, HG et al. "Myocardial infarction in rats: effects of metabolic and pharmacologic interventions" Basic Res. Cardiol 84 (1989) 332-343.
International Search Report and Written Opinion, Related PCT/US09/31910.

* cited by examiner

*Primary Examiner* — Elli Peselev
(74) *Attorney, Agent, or Firm* — Wong, Cabello, Lutsch, Rutherford & Brucculeri, LLP

(57) ABSTRACT

Provided herein are methods and formulations for preventing or ameliorating progression to chronic heart failure subsequent to cardiac stress, including as a consequence of myocardial infarction (MI), coronary artery disease, hypertension, cardiomyopathy, myocarditis, valvular regurgitation, severe lung disease, and/or severe anemia of chronic disease, by administration of one or more rate-limiting precursors to the synthesis of ATP. In one embodiment the ATP precursor is a pentose selected from one or more of ribose, D-ribose, ribulose, xylitol, xylulose, and a 5-carbon precursor of ribose.

11 Claims, 5 Drawing Sheets

M-Mode Echocardiography

A. Baseline before MI

Figure 1:
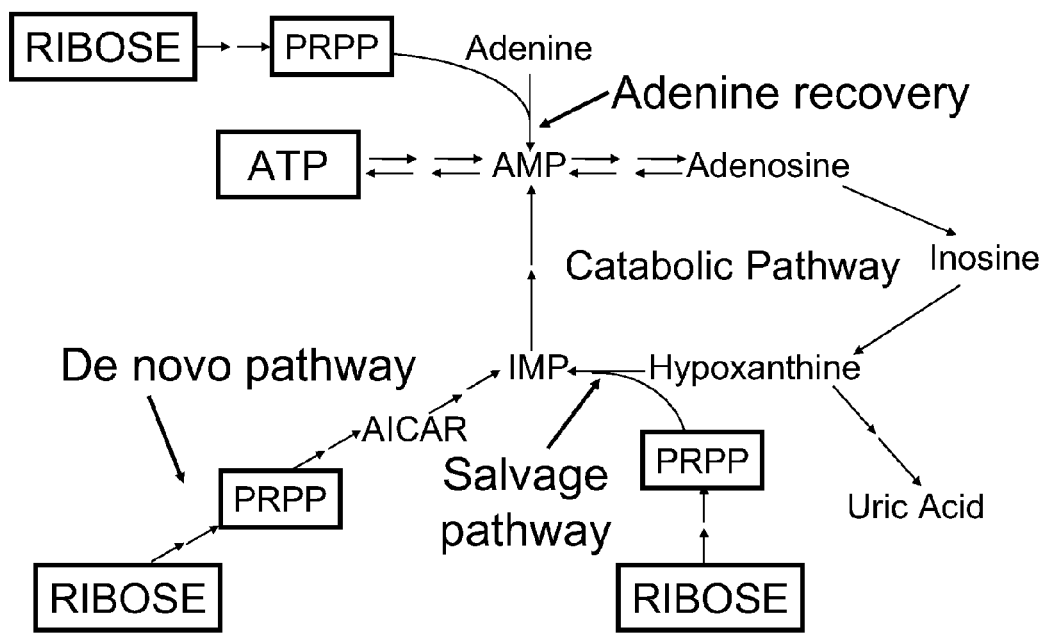

B. Untreated – 4 weeks after MI

Control

EDV 0.94 ml
ESV 0.64 ml
SV  0.30 ml
EF  32.1 %

Ribose

EDV 0.42 ml
ESV 0.23 ml
SV  0.19 ml
EF  44.5 %

METHODS AND COMPOSITIONS FOR INHIBITING PROGRESSION TO CHRONIC CARDIAC FAILURE

CROSS REFERENCE TO RELATED APPLICATIONS

This application is the §371 U.S. National Stage of International Application No. PCT/US2009/031910, with an International Filing Date of 23 Jan. 2009, which claims priority based on U.S. Provisional Application No. 61/023,712, filed Jan. 25, 2008, the disclosures of which are incorporated herein by reference in their entireties.

FIELD OF THE INVENTION

This invention relates generally to compositions and methods for reducing progression to heart failure as a consequence of cardiac stress.

BACKGROUND OF THE INVENTION

Without limiting the scope of the invention, its background is described in connection with the existing understanding of heart failure. The myocardium, when stressed from a variety of causes including myocardial infarction (MI), coronary artery disease, hypertension, cardiomyopathy, myocarditis, valvular regurgitation, severe lung disease, and severe anemia of chronic disease, may develop increasing dysfunction and go on to apoptosis of cardiocytes and a detrimental remodeling of the myocardium. This progression ultimately results in the clinical entity of chronic heart failure (CHF), also known as chronic cardiac failure (CCF) or chronic congestive heart failure. The present invention is focused on an important distinction between the inciting cardiac lesion, whether myocardial infarction, valve disease etc., and the remote, often normal, myocardium. It is this remote myocardium that suffers compensatory stress and which descends into failure. Also of importance to the present invention is a recognition that the dysfunction which may affect the normal or remote myocardium is often progressive in nature. Although this progression has been well documented and recognized, what controls it is unknown According to national surveys, an estimated 4.8 million Americans have congestive heart failure, divided equally between men and women. Of these, almost 1.4 million are under 60 years of age. Prevalence of CHF is increasing substantially with an estimated 400,000 new cases each year according to National Heart, Lung, and Blood Institute (NHLBI) statistics. As CHF is the end stage of cardiac disease, half of the patients diagnosed with CHF will be dead within 5 years. Increasing prevalence, hospitalizations, and deaths have made CHF a major chronic problem in the United States and the most common cause of hospitalization.

CHF treatments are currently limited to alleviating symptoms of existing heart failure including through significant life style changes, medications such as diuretics and ACE inhibitors which can have significant side effects, and surgery. All current treatments for heart disease which do not treat the inciting lesions themselves (i.e., coronary artery stents, valve replacements, etc.) are secondary in nature. Some medications, for example, will produce dilation of the vessels in the body and, therefore, reduce the resistance to blood flow which the heart must overcome. This does not treat the cardiomyocytes directly but it does reduce the work the heart must do, providing secondary benefit. No measures currently exist, however, that directly prevent or even ameliorate root causes of the progression to CHF.

From the foregoing it is apparent the there is a need in the art for compositions and methods for preventing or significantly slowing the progressive damage to the myocardium which results in CHF. The invention described provides a novel method and compositions which significantly reduces the progression to CHF in individuals at risk for development.

BRIEF SUMMARY OF THE INVENTION

The present invention is directed to preventing or ameliorating progression to chronic heart failure subsequent to cardiac stress by administration of one or more rate-limiting precursors to the synthesis of ATP. In one embodiment the ATP precursor is selected from one or more of adenosine, adenine, inosine, 5-amino-4-imidazolcarboxamide riboside, and a pentose. In one embodiment the pentose is selected from one or more of ribose, D-ribose, ribulose, xylitol, xylulose, and a 5-carbon precursor of ribose.

In one embodiment the cardiac stress results from myocardial infarction (MI), coronary artery disease, hypertension, cardiomyopathy, myocarditis, valvular regurgitation, severe lung disease, and/or severe anemia of chronic disease.

In one embodiment of the invention, progression of normal, or nearly normal, myocardium to chronically damaged and failing heart tissue is prevented or limited by administration of one or more rate-limiting precursors to the synthesis of ATP in such a way that the precursors are continuously available for a prolonged period in order to prevent return to the continuing progression of injury, subsequent remodeling and CHF. In one embodiment, the prolonged period where rate-limiting precursors to the synthesis of ATP are continuously available by parenteral administration and preferably by continuous intravenous infusion for at least a period of acute hospitalization. In such embodiments, the prolonged period is at least 3 days, followed by oral administration for at least 3 weeks. In other embodiments the intravenous treatment is extended to 7 to 14 days or longer depending on the status of the individual and their individual response to therapy. In such embodiments, the patient, if discharged but still considered to have some degree of dysfunction, the patient is discharged with an I.V. line in place, which is connected to a source of rate-limiting precursors to the synthesis of ATP. The period of oral administration begins at least upon cessation of parenteral treatment and continues for 3 weeks or more. Treatment by oral administration is preferably continued for 3 to 6 months, depending on preservation of LV function.

In one embodiment of the invention, rate-limiting precursors to the synthesis of ATP are provided either by bolus injection or by i.v. administration as soon as an acute myocardial stress is strongly suspected and warrants insertion of a venous line in the patient. This acute treatment may be begun in an ambulance or in the emergency room and continued for the aforementioned prolonged period. Thus, in one embodiment of the invention, an emergency or crash-cart kit is provided including a premixed formulation of one or more rate-limiting precursors to the synthesis of ATP. In one particular embodiment the kit contains a volume of solution sufficient to provide a "loading dose" equivalent to about 1 ml/kg of a 5% solution of a pentose moiety, preferably ribose, over 1-2 hours. Following the loading solution administration, a continuous infusion is begun of a pentose solution equivalent to about 0.2 to about 0.4 ml/kg/hr of a 5% solution thereafter for as long as an intravenous line is in place during hospitalization.

In one embodiment the one or more rate-limiting precursors to the synthesis of ATP are made continuously available by parenteral infusion. In one embodiment, a parenteral infusion set is provided including the rate-limiting precursors to the synthesis of ATP as well as instructions for delivery. In one embodiment, a continuous infusion pump is provided for long term administration of the rate-limiting precursors to the synthesis of ATP. Following infusion, one or more rate-limiting precursors to the synthesis of ATP are delivered by oral administration.

In another embodiment, the one or more rate-limiting precursors to the synthesis of ATP are given initially intravenously to insure continuous high levels and overcome any difficulty to eating caused by the inciting cardiac event (e.g. MI) and later given orally when hospitalization is no longer necessary.

Also provided herein are parenteral solutions including one or more rate-limiting precursors to synthesis of ATP for use in preventing myocardial stress from progressing to chronic heart failure (CHF) and which are adapted to be administered continuously for at least a period of hospitalization to a patient at risk for development of CHF. In one aspect the rate-limiting precursor to synthesis of ATP is selected from one or more of adenosine, adenine, inosine, 5-amino-4-imidazolcarboxamide riboside, and a pentose moiety. The pentose moiety is selected from one or more of ribose, D-ribose, ribulose, xylitol, xylulose, and a 5-carbon precursor of ribose. In one aspect, the parenteral solution is formulated for delivery at a dosage equivalent to about 0.2 to about 0.4 ml/kg/hr of a 5% solution of a pentose. In certain embodiments, the parenteral solution further comprises a glucose solution.

A parenteral loading dose solution for use in preventing myocardial stress from progressing to chronic heart failure (CHF), wherein parenteral loading dose solution comprises a pentose formulated for delivery of an amount of pentose equivalent to about 1 ml/kg of a 5% solution given over about 1-2 hours.

In one embodiment of the invention, progression of damage in tissues bordering an area of infarction in a myocardial infarction patient are reduced and at least a portion of the at risk border zone is allowed to recover, thereby reducing the ultimate size of the infarction, by administering a composition including an effective amount of one or more rate-limiting precursors to the synthesis of ATP. The ATP precursor is selected from one or more of adenosine, adenine, inosine, 5-amino-4-imidazolcarboxamide riboside, and a pentose moiety.

In one embodiment of the invention, an effective amount of one or more rate-limiting precursors to the synthesis of ATP is provided to prevent functional consequences resulting from stress on the relatively normal remaining portions of the ventricle following a MI. In one embodiment, the functional consequence is mitral valve regurgitation. In one embodiment the relatively normal remaining portions of the ventricle are the papillary muscles. In one embodiment an effective amount of one or more rate-limiting precursors to the synthesis of ATP are administered to reduce the occurrence of arrhythmias which arise in the stressed normal remaining tissue following a MI.

For a more complete understanding of the present invention, including features and advantages, reference is now made to the detailed description of the invention along with the accompanying figures:

BRIEF DESCRIPTION THE DRAWINGS

FIG. 1 illustrates the role of ribose in adenine nucleotide metabolism. The irreversible breakdown (catabolism) of AMP to small compounds that are washed out of the cell is shown centrally. The three pathways of resynthesis of AMP are shown leading to it. The most important seems to be the de novo pathway, but all three require ribose as the essential compound.

Figure 2:
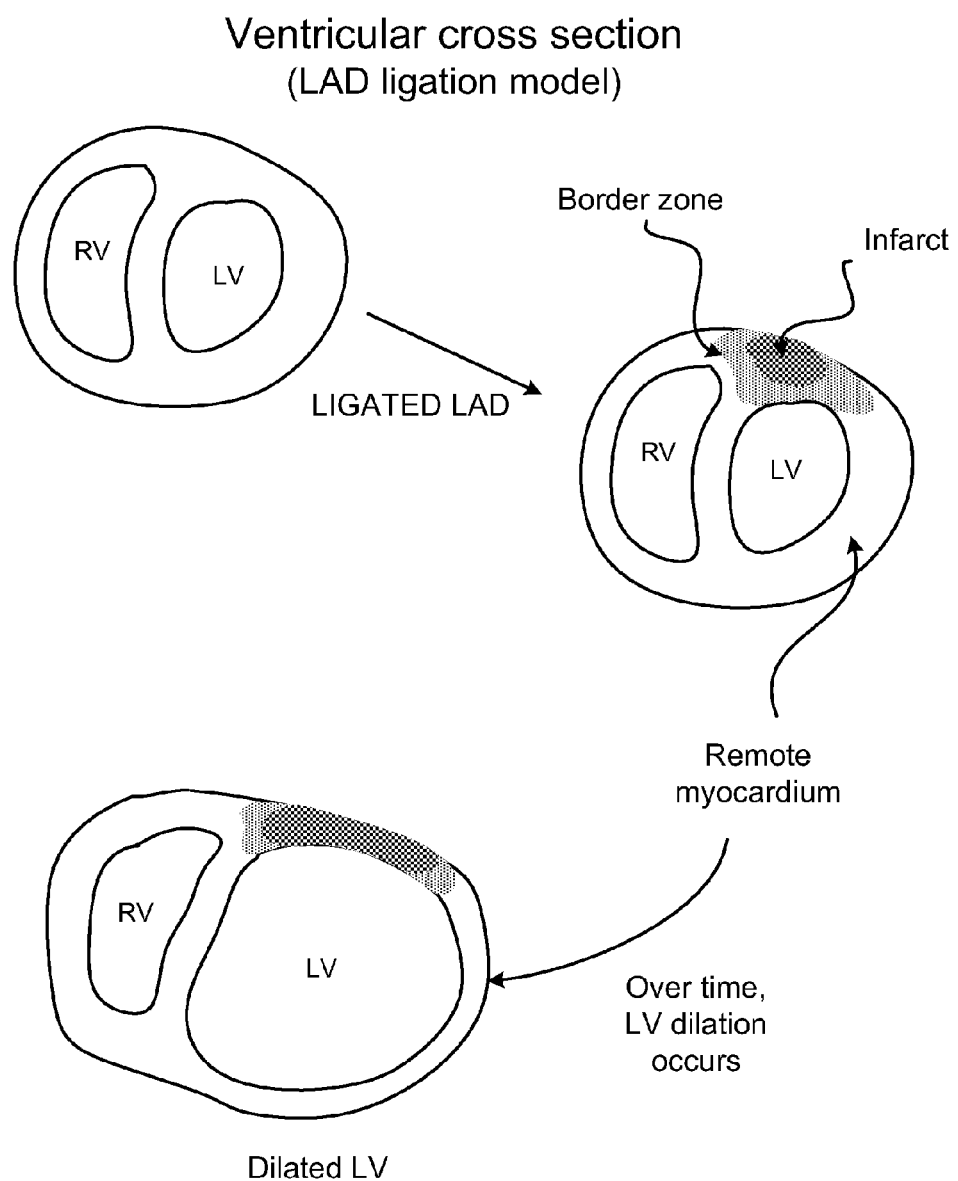

FIG. 2 represents the progression to CCF resulting from an earlier infarct. This carton depicts the LAD artery ligation procedure with the resulting infarction (death) and surrounding border zone areas. With time, as LV function decreases, the LV begins to dilate and progresses to CHF.

Figure 3:
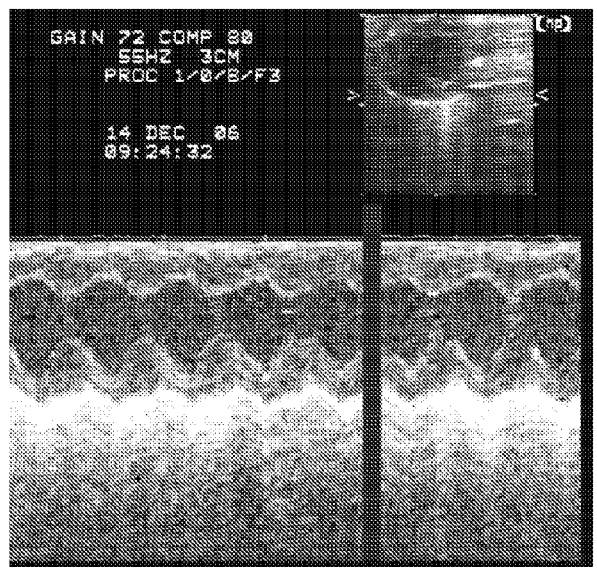
Figure 3:
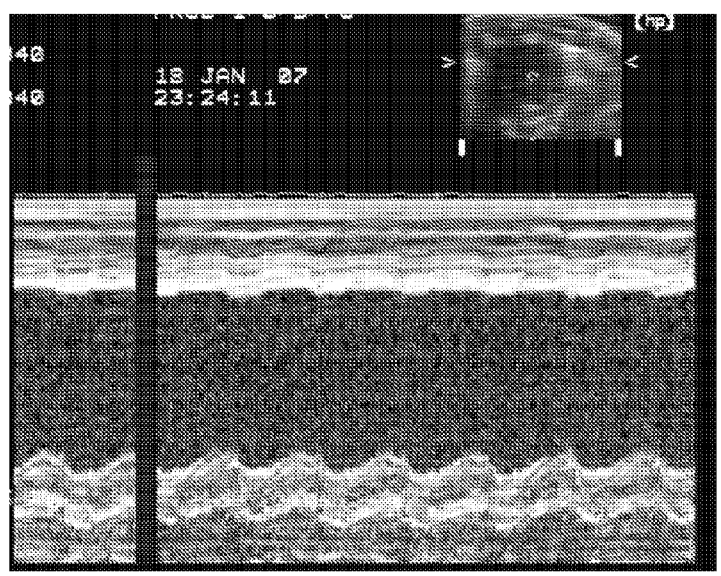

FIG. 3 represents M-Mode echocardiographic images of a rat heart at baseline and after CHF has begun to develop. These echocardiograms, which represent a slice of a LV, show the wall thinning and the dilation of the cavity (the dark, wide band centrally) as the ventricle begins to fail (control animal without ribose infusion).

Figure 4:
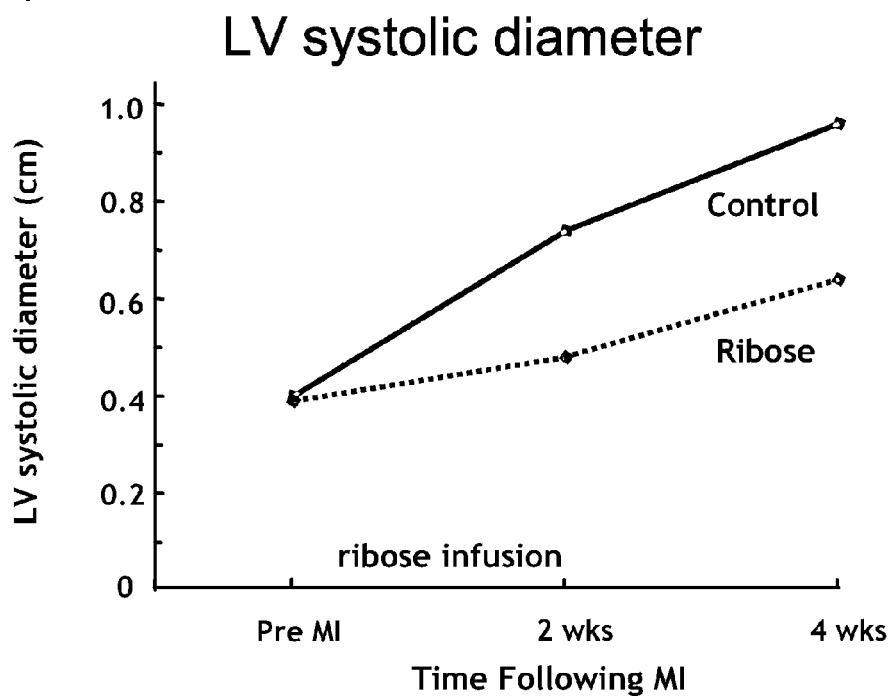

FIG. 4 depicts the effects of ribose on LV systolic diameter in a rat model of CHF. The 2-D echo-derived LV dimensions at the end of systole (contraction) are shown for ribose-treated and control animals. This revealed that during the 2 weeks of ribose infusion, there was little reduction in contractility. During the next 2 weeks, however, some decrease in function occurred which supports the benefit of longer-term therapy.

Figure 5:
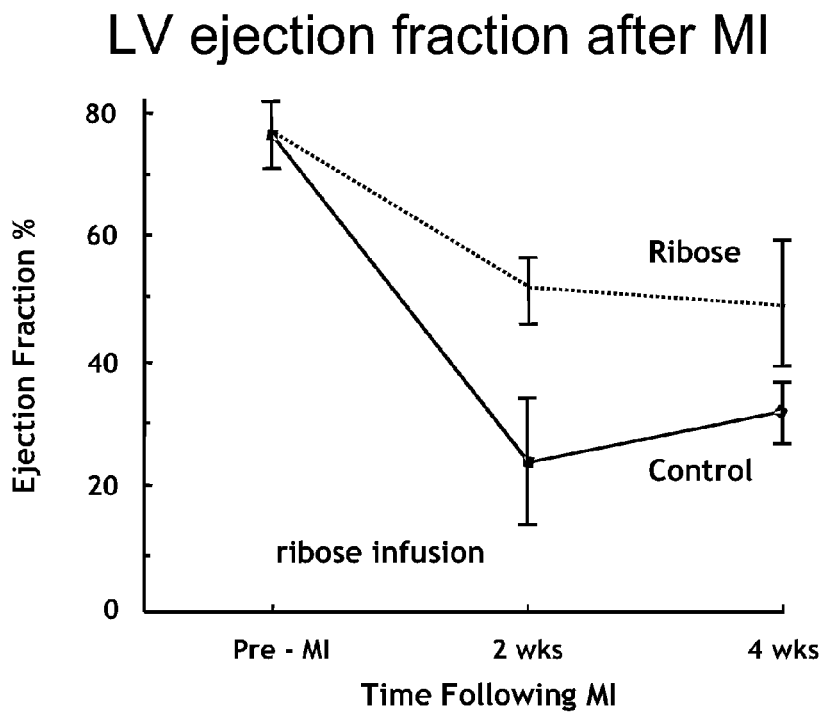

FIG. 5 depicts the effects of ribose on LV ejection fraction in a rat model of CHF. The ejection fractions (EFs) of the two groups are plotted and reveal the clear benefit of the longer-term therapy.

Figure 6:
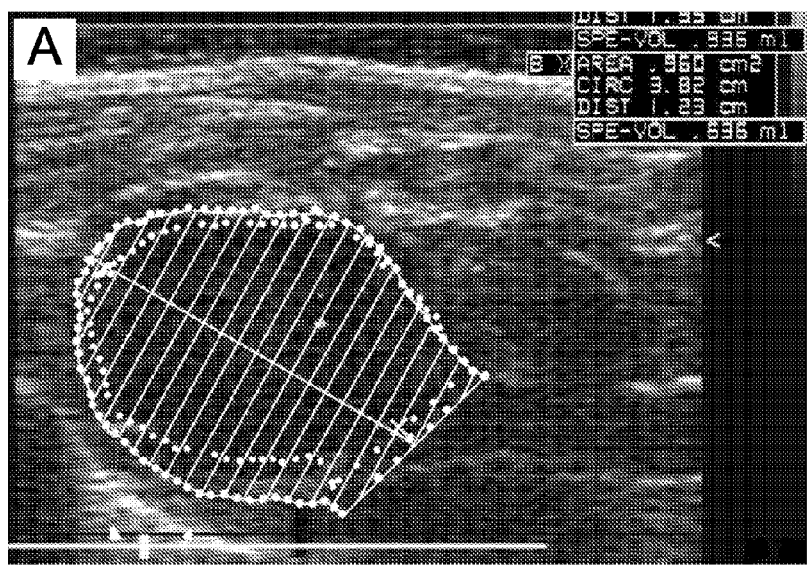
Figure 6:
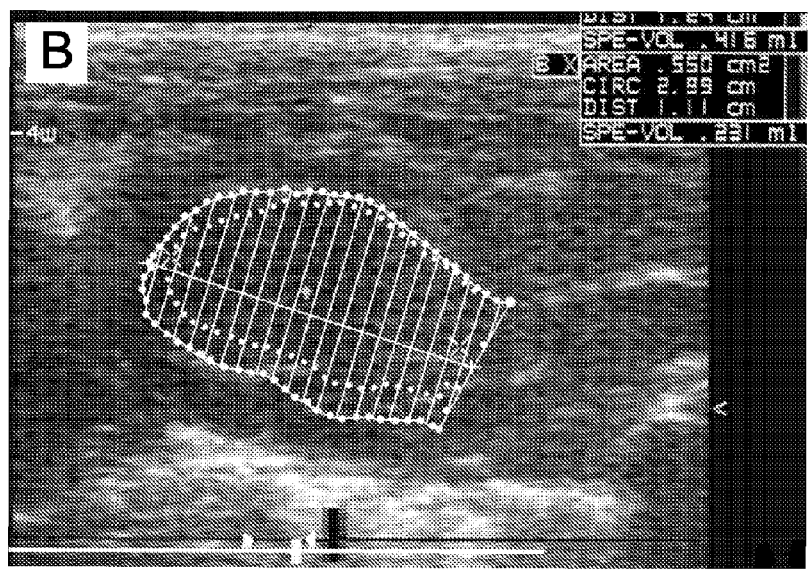

FIG. 6 depicts the effects of ribose on EDV, ESV, SV and EF in a rat model of CHF. Representative 2-D images of a LV during systole and diastole are presented. By modeling calculations, the volumes both at full relaxation and contraction as well as the EF can be determined. The significant LV dilation with reduced function in the untreated animal is apparent.

DETAILED DESCRIPTION OF THE INVENTION

While the making and using of various embodiments of the present invention are discussed in detail below, it should be appreciated that the present invention provides many applicable inventive concepts which can be employed in a wide variety of specific contexts. The specific embodiments discussed herein are merely illustrative of specific ways to make and use the invention and do not limit the scope of the invention.

ABBREVIATIONS: The following abbreviations are used throughout this application:

| | |
|---|---|
| ADP | adenosine diphosphate |
| AMP | adenosine monophosphate |
| ATP | adenosine triphosphate |
| CHF | chronic heart failure |
| EDV | end-diastolic volume (maximal filling) |
| EF | ejection fraction |
| ESV | end-systolic volume (maximal ejection) |
| G6PDH | glucose-6-phosphate dehydrogenase |
| LAD | left anterior descending |
| LV | left ventricular |
| MI | myocardial infarction |
| PRPP | 5-phosphoribosyl-1-pyrophosphate |
| RM | remote myocardium |
| SV | stroke volume |

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

As used herein the term "parenteral infusion" means other by a gastrointestinal route of administration. Examples include by subcutaneous, intramuscular and intravenous.

For purposes of the present invention, "rate-limiting precursors to the synthesis of ATP" include adenosine, adenine, inosine, 5-amino-4-imidazolcarboxamide riboside, as well as pentose moieties. For purposes of the present invention, the term "pentose moiety" means a monosaccharide, including but not limited to, ribose, D-ribose, ribulose, xylitol, xylulose, and any 5-carbon precursor of ribose.

Ribose is a 5-carbon sugar that is the foundation for several vital functional classes of molecules use ribose (or deoxyribose) as the foundation for active groups to form informational (RNA and DNA), messenger (cAMP and cGMP), certain vitamins, cofactors, the NAP, NADP, NADPH acceptor molecules, and the energy transporting nucleotides (ATP and ADP). The importance of these compounds to the cell can not be overstated. Thus, ribose is the vital structural backbone of critical cellular compounds formed by adding the active moieties (either purines or pyrimidines and the phosphate groups) to it or to its more active form 5-phosphoribosyl-1-pyrophosphate (PRPP) as depicted in FIG. 1. Therefore, the production of these vital cellular constituents requires an adequate supply of these components including ribose, purines and pyrimidines and phosphate moieties. Among these, ribose, is the rate-limiting component.

Ribose provides the foundation for the synthesis of these fundamental cellular compounds. Because these compounds are in relatively constant supply in cells and are not consumed (turnover is slow), the need for ribose is relatively predictable and not marked by sudden large surges in synthetic requirements. It is not surprising, therefore, that the synthetic rate of these important compounds is relatively low and can not increase very much. Analysis of the nucleotide synthetic rate, moreover, has shown that ribose is the rate-limiting precursor. Ribose is produced from the commonly present 6-carbon sugar glucose by the coupled enzyme which includes G6PDH and accomplishes the decarboxylation. Because of the normally limited need for ribose and the heavy use of glucose in glycolysis and energy production, the cell severely limits the diversion to ribose by this rate-controlling step.

For the heart, however, the situation is more complex. Nucleotide synthesis has much smaller bursts of activity and significant deficiency states related to this synthesis are unlikely to occur. The myocardium is particularly vulnerable to the loss of ATP by stress and the subsequent breakdown of the resulting AMP to its component parts, producing in effect a deficiency in ribose.

In times of stress to the heart, the concentrations of ATP will fall when its production from ADP (and AMP) does not meet demand, as would be expected. Of much more significance, and unexpected when it was discovered, is the further response of myocardial energy metabolism to this situation, principally the irreversible breakdown of AMP. Recovery from stress then requires a resynthesis of a greatly increased amount of AMP (which can be charged to ATP) but this is normally a very slow process. The resulting AMP was found not to accumulate to any degree and, instead, is broken down to small components which are washed out of the heart, insuring that the ATP levels will not easily recover.

As noted above, the availability of ribose-5-P and the form, PRPP, is what limits AMP synthesis. The phosphate groups are typically in abundance and, although the purine base, adenine in excess has been used experimentally in the recovery from global ischemia, at best, it seems to have a minor effect. Ribose is the rate-limiting compound but, unfortunately, even under severe stress, the myocardial cell has only a limited capacity to increase ribose-5-P synthesis and G6PDH activity. As a result, the relatively slow synthesis of ribose-5-P and, therefore, of AMP, makes the recovery of ATP levels a slow process, requiring days to recover fully after a moderate insult.

Because heart disease itself is a chronic condition, it typically imposes a relatively continuous stress, and a slow fall in ATP may result with little opportunity to recover. Because recovery requires the slow synthesis of AMP, in a practical sense, a significant deficiency of ribose is produced. In these settings, the present inventor recognized that the synthesis of AMP is most limited by the availability of ribose and, that continued efforts to generate AMP would result in a significant deficiency of ribose. The present inventor further proposed that this ribose deficiency not only limits recovery but is a significant cause of progression to CHF. Thus, in these settings, a hypothesis was tested that providing adequate supplies of ribose would be effective in preventing, or at least slowing, a progression into CHF. The confirmation of this hypothesis disclosed herein provides a mechanism to prevent the development of CHF, which is clearly a much more effective strategy than trying to ameliorate the resulting condition.

As detailed herein, by far the most important direct purpose of pentose sugar administration will be to increase the synthetic rate of AMP, which will, in turn, be fully charged to ATP by the oxidation of the various fuels (sugars, fatty acids and amino acids) in the cell. By far the most significant consequence then of administration of a pentose sugar such as ribose, a simple 5-carbon sugar, is to raise cellular energy (ATP) levels. The mechanism by which the ATP levels are increased is only through the enhanced synthesis of AMP. Once AMP is synthesized, the energy produced by cell metabolism is easily transferred to AMP and ADP, resulting in the fully charged ATP.

Ribose is used by the cell only for the synthesis of the vital molecules previously listed and as a result, the cell will not significantly consume or oxidize ribose as they do other sugars such as glucose. Ribose is not broken down to provide energy to convert ADP to ATP. The biochemical pathways of adenine nucleotide metabolism via ribose and ATP are depicted in FIG. 1.

Chronic heart failure (CHF) has become epidemic in numbers in the US and other industrialized countries. Many different insults to the heart (infarcts, diseased valves, cardiomyopathies, etc.) can lead to CHF, the most common being coronary artery disease which produces severe ischemia and infarction of the areas previously supplied by the occluded vessels. Despite the many different forms of the inciting heart disease, the failing heart has many similarities. A hypothesis is that the early subcellular consequences of these various lesions on the myocardium are similar as is the pathway to and the progression of failure. As noted, the remote myocardium which fails may be essentially normal, apart from the inciting cardiac event. The failing heart has been extensively studied to elucidate the sub-cellular changes which occur nevertheless, it is not known what sets in motion the pathway to failure. It is agreed, however, that CHF is often a progressive disease even if no new heart lesions occur. On this basis, the present inventor proposed that a common pathway is activated and that the trigger persists.

The present inventor undertook to discriminate between two possible general mechanisms for beginning the path to failure, expecting this understanding would suggest one or more effective methods of therapy. The first one being that an excessive stress placed on the remaining normal ventricle gradually breaks down the contractile apparatus. Indeed, some authorities on CHF believe this is the primary mechanism and that the stress on the remaining myocardium begins a progressive breakdown of the contractile apparatus of the myocardial cells leading to CHF.

An alternative hypothesis, advanced and tested by the present inventor as disclosed herein, provides that stress placed on the heart, or portions thereof, result in a greater energy demand on the normal tissue than can be supplied. By the biochemical response of the myocardium, as discussed earlier, the ATP levels gradually fall and this in turn leads to the decreased functioning of the myocardium. The next part of this theory states that it is the concentration or level of ATP that is of particular importance to the various functions which occur in the myocardium. There is evidence for this proposal, including among others that the uptake of calcium by the sarcoplasmic reticulum, which governs diastolic function, is directly affected by ATP levels.

Under normal conditions, ATP levels are remarkably stable despite the heart using more energy per weight than any other organ. The energy needed requires the turnover from ADP to ATP and back (energy production and utilization) to occur 10,000 times/day for each molecule. Under sufficient stress, however, the energy production can not keep up with demand and the ATP levels fall and, momentarily AMP levels rise. If the duration of stress is short, the AMP can be recharged and ATP levels will recover. With heart disease, however, the stress persists and the enzymes which break down AMP are activated and reduce it to small components which are washed out of the cell. The pathophysiologic explanation disclosed herein is that the stress of heart disease leads first to an irreversible breakdown of AMP which requires new synthesis of AMP to maintain adequate ATP levels. Because this stress will predictably continue, recovery will not occur and a further slide in ATP levels may result if the rate-limiting component, ribose, is not provided.

Based on an understanding of the underlying pathogenesis disclosed herein, the treatment provided by this invention, therefore, will have to be for a relatively prolonged period and will in most cases exceed the period of an acute injurious episode such as immediately following a myocardial infarction and, optimally, the treatment will be continued until the remote myocardium can compensate for the stress or until the stress is removed.

For example, in the example described herein, ribose was given for two weeks, during which time the remaining (remote) normal myocardium was under stress. The border zone adjacent to the infarct was also put in jeopardy of going on to infarction. The continued infusion of ribose was done to prevent the ATP levels in the normal myocardium from falling to levels which would significantly decrease function. In addition, the ribose infusion was given to prevent the border zone from going on to infarction and, moreover, to allow a portion to recover.

Consequently, the present therapy is specifically directed to the energy metabolism of the remaining functional tissue. By preventing the fall in energy levels which will otherwise occur, the treatment limits or prevents the dysfunction which will result and by minimizing the increasing cycle of severity, significantly reduces the longer term consequence of prolonged cardiac stress, which is chronic heart failure. Of course, a similar benefit will be found in tissue which is not normal but maintains a degree of function and its progression to failure can be slowed. Finally, the improved energy levels and function of the remote myocardium will also favorably affect the recovery of at least part of the neighboring border zone.

In one embodiment, treatment is initiated in patients who have just had an MI or developed other heart lesions and diseases. Because this invention demonstrates that the primary event controlling the pathway to failure is a fall myocardial energy levels rather than the usual explanation that this begins with an initial and progressive breakdown of the cellular contractile apparatus, this treatment is applicable to a variety of heart lesions expected to produce CHF. Because of the importance of heart disease and the common progression to CHF, this represents a significant advance. Treatment with a pentose, such as for example ribose, provides a direct treatment of the sub-cellular myocardial changes that lead to heart failure. In one embodiment of the invention, pentose is administered as an additive to other treatments. There is no known down-side to raising myocardial (and other cells) energy levels.

In one embodiment of the invention, pentose is administered chronically in a patient having a condition that presents a known risk of progression to CHF. As chronically administered, the pentose: 1) will directly correct and prevent the central problem of reduced energy stores, 2) is additive to existing therapies, 3) is only positive in effect, i.e. increases synthesis of AMP and related molecules, 4) does not inhibit other biochemical or physiological events, and, very importantly, 5) has virtually no risk.

Many investigators have attempted to show that specific precursors will block the fall in ATP levels or will augment ATP recovery in severe and acute situations, such as ischemia and very unfavorable situations such as the creation of a significant cardiac lesion, such as valve disruption, when one expected consequence would be a fall in ATP levels. Adenosine, adenine, inosine, 5-amino-4-imidazolcarboxamide riboside and ribose are some of the ATP precursors that have been studied to acutely increase ATP synthesis. Most studies were of short duration, and directed to amelioration of the acute injury. The one exception was the longer term oral clinical study, cited below, which assessed only a few secondary function parameters. The significant studies were only directed at improving an acute cardiac problem and not to reducing or preventing the severe consequences of CHF. Consequently, in these acute studies, only partial ATP recovery was found, and none accomplished complete return of ATP levels once severe depression had been induced. Moreover, none were directed to preventing the progression to failure that includes dysfunction of the remaining myocardium, which leads to the ominous wall thinning and ventricular dilation that are the clinical hallmarks of CHF and which indicate cell death (apoptosis) and replacement fibrosis (remodeling) as the condition becomes chronic. It is these changes, however, both physiological and subcellular, which define CHF which we seek to prevent or, at least, greatly ameliorate.

For example Seifart et al. (*Basic Res. Cardiol.* 75 (1980) 57) studied isolated, electrically-driven guinea pig atria in which adenine and ribose were found to "inhibit the loss of cardiac adenine and pyridine nucleotides during anoxia." In this study the isolated atria were stabilized for an hour then subjected to nitrogen to cause 2 hours of anoxia (blood flow but no oxygen), not ischemia (no blood flow and no oxygen). The addition of adenine and ribose after one hour of anoxia reduced the further fall in ATP levels during the next hour of anoxia. No investigation was made of the ability of adenine and ribose to restore fallen ATP levels.

H. G. Zimmer (*Science* 220 (1983) 81) reported a study in which ATP levels were shown to be maintained for 24 hours in rats treated with ribose after being given a toxic dose of isoproterenol and subjected to constriction of the abdominal aorta. The combined stresses of catecholamine stimulation and increased blood pressure on the heart resulted in lowered myocardial ATP levels in controls. This study focused on acute stresses and Zimmer concluded that "the reductions in ATP and total adenine nucleotides were prevented" by this treatment. The ability of ribose to prevent any consequences after 24 hurs or to enhance recovery after an ATP fall had occurred were not tested.

In a later study, Zimmer (*Basic Res. Cardiol.* 84 (1989) 332) reported that continuous i.v. administration of ribose beginning prior to coronary artery ligation and continuing for up to 48 hours in a rodent MI model was able to reduce the fall of ATP in the nonischemic myocardium determined at the first (24 hr) time point. For the next 3 days, ATP recovery in both ribose-treated and control rats increased at the same rate. It should be noted that the ribose dosage was extremely large (a 70 kg man would receive 336 gms daily intravenously). Among the function parameters studied (under general anesthesia and with a tracheostomy in place), only the post-MI rise in LV end-diastolic pressure was reduced (helped) by the ribose infusion. Zimmer believed that pretreatment was necessary to achieve the benefit, however, in the commonly occurring MI in humans, treatment can only occur after the event. He further speculated that the basic mechanism of the LVEDP dysfunction resulted from changes in the contractile apparatus or "the stretch of myocardial fibers." This is one of the two general possibilities, although the evidence presented in this application strongly indicates a fall in ATP levels is the primary event.

The present inventor previously discovered that administration of ribose was able to reduce the period of recovery from an acute ischemic episode. Only the recovery from a complete global insult such as occurs during heart surgery was studied. There was no normal tissue in these hearts to study and the longer-term consequences were not considered. See Foker U.S. Pat. Nos. 4,605,644 and 4,719,201.

Finally in a prospective, double-blind, randomized, crossover design study, the effect of oral D-ribose supplementation on cardiac hemodynamics and quality of life was studied in 15 patients with chronic coronary artery disease and CHF. In patients with existing CHF, 3 weeks of oral D-ribose resulted in an improvement in some of the echo markers used to assess LV filling. The left atrial contribution to left ventricular filling was improved (40±11 vs. 45±±9%, P=0.02) and a smaller left atrial dimension (54±20 vs. 47±18 ml, P=0.02) and a shortened E wave deceleration (235±64 vs. 196±42, P=0.002) were seen by echocardiography. Further, D-ribose also led to an improvement of the patient's quality of life by questionnaire (417±118 vs. 467±128, P< or =0.01). In summary, this study showed that the administration of ribose to patients who already had CHF could produce small but, statistically significant, improvements in certain echo markers of diastolic function and in the responses to a quality of life questionnaire. The study provided neither information nor speculation on the possibility of reducing or preventing the events which start and continue the pathway to CHF.

The ability of a nucleotide precursor to prevent the progression to CHF has not heretofore been shown. Progression to heart failure is a long-term problem that takes over 4 weeks to develop in rats and months to years in humans. The present inventor has now shown that ribose can prevent progression to heart failure in a rat model that is analogous to the development of heart failure in humans.

The following examples are included for the sake of completeness of disclosure and to illustrate the methods of making the compositions and composites of the present invention as well as to present certain characteristics of the compositions. In no way are these examples intended to limit the scope or teaching of this disclosure.

EXAMPLE 1

Although believed to be applicable to several different precipitating causes of CHF, the present inventor initially chose a myocardial infarction model because it would allow the effects of the infarct on the normal remaining myocardium to be studied without confounding factors, particularly the presence of disease in the tissues studied. The experiment involved long-term infusion of ribose into rats having had a coronary artery ligated to produce a MI.

An important consequence of an MI is that the uninvolved, often normal, remote myocardium (RM) must assume the entire workload of the ventricle. This additional strain on the RM has been shown to lead to apoptosis and remodeling and the dilation of the LV that is characteristic of CHF. The subcellular events which control and set in motion, the progression to CHF were heretofore unknown. The present inventor hypothesized that the progression begins when the remaining normal myocardium (RM) must assume the entire cardiac load, in effect a large increase for the RM, producing an unfavorable myocardial energy supply/demand ratio which leads to depressed myocardial energy levels. Moreover, because of the continuous nature of the stress imposed, there is essentially no opportunity to recover. As a result, the continued breakdown of AMP with further erosion of ATP levels occurs. Studies to understand this progression in a myocardial infarction (MI) model were undertaken. The hypothesis that a fall in RM energy levels, including myocardial ATP, leads to decreased function was tested by infusing ribose in a rat MI model. A rat myocardial infarction model involving (left anterior descending (LAD) artery ligation) was utilized. In this model the RM must produce the entire cardiac output and left ventricular (LV) dysfunction develops as depicted in FIG. 2 and in the results depicted in FIGS. 3-6.

On a molecular level, stress results in an energy supply that is less than the demand. Consequently, ATP levels fall and catabolic pathways are activated resulting in increased breakdown of the ATP precursor AMP and the washout of the resulting components. From acute stress models of recovery (i.e. global ischemia) ATP recovery takes days after the insult. ATP recovery proceeds by the synthesis of AMP and conversion to ATP. The first phase, the synthesis of AMP, is by far, the slowest and is limited by the conversion of glucose-6P (by the coupled G6PDH enzyme) to ribose-5P. Administration of ribose bypasses the G6PDH step and speeds ATP recovery by at least 10 fold.

Methods: Male Lewis rats (250-300 g, n=12) were evaluated by initial baseline 2D guided M-mode echocardiographic analysis using an HP SONOS 1550 system. The echocardiography included short axis views and EF by cubed formula, analyzing the variables of LVdd, LVsd, RM wall thickness, EF and SF. Each animal had an osmotic mini-pump (Durect, Inc.) implanted. Animals underwent ligation of the left anterior descending coronary artery by to produce an anterior wall MI at 1-2 days after pump placement and received continuous venous infusion of 0.9% NaCl solution (at 30 µl/kg/hr) with or without 2.5% D-ribose (N=6 for each group) via the implanted osmotic mini-pump for 14 days.

Echocardiographic analysis was performed 2 and 4 weeks post-MI to assess changes in function by ejection indices (ventricular contractility, ejection and shortening fractions), chamber dimensions, and wall thickness. FIG. 3 depicts the M-mode echocardiographic appearance of a rat heart in which post MI CHF has developed.

Results: Important and clinically relevant indices of function were chosen. FIG. 4 depicts the results of long-term ribose treatment on LV systolic diameter after an MI. FIG. 5 depicts the results of long-term ribose treatment on LV ejection fraction after an MI. FIG. 6 depicts the results of ribose treatment on EDV, ESV, SV and EF by 2D long Axis volume tracing. The results showed that ribose treatment better preserved contractility (EF, SF) and increased wall thickness compared to the untreated animals. Very importantly, ventricular dilation, the hallmark of CHF was significantly reduced. These data show (1) the RM shows a significant decrease in function four weeks following an MI, and (2) ribose infusion prevents, to a significant degree, the dysfunction. The benefit of ribose suggests the increased workload on the RM produces an unfavorable energy supply/demand ratio which results in lower myocardial energy levels.

It was determined that in a global ischemia and reperfusion model that ribose infusion will greatly enhance return of myocardial ATP levels and function. Because ribose is the rate-limiting precursor to adenine nucleotide synthesis and is not itself a fuel source, increased AMP synthesis was concluded to be the reason for the enhanced recovery.

By all indices, as summarized in Table 1 below, the function of the RM was better maintained with ribose treatment following an anterior MI.

while a lesser effect was shown to have persisted by 4 weeks after the MI. On this basis, in one embodiment of the invention, pentose therapy includes continued intravenous therapy to produce high levels during the time of recovery from the acute event (e.g. an MI) and when oral intact may be very limited, followed by oral pentose for as long as needed. In one embodiment of the invention an intravenous therapy is provided including administration of a solution of approximately 5% ribose and approximately 5% glucose (the glucose is added to preserve blood glucose levels during this period of limited oral intake).

In one embodiment, a "loading dose" is provided equivalent in dosage to approximately 1 ml/kg for a 5% ribose solution is given over 1-2 hours, followed by a dosage equivalent to about 0.2 to about 0.4 ml/kg/hr of a 5% ribose solution thereafter. In a preferred embodiment the ribose solution is supplemented with glucose, such as for example 5% glucose, to preserve blood glucose levels. Upon discharge, the patient would be converted to oral dosage of about 10-20 grams of ribose, typically in divided doses. The amount of ribose is given above and it is anticipated that other pentoses would be given at the same rate or slightly greater to compensate for the inefficiencies in the conversion to ribose.

As with other medications, the amount, route and duration will be adjusted by several factors. The first consideration in the duration of intravenous therapy would be the length of hospitalization and this has steadily declined over the past few decades. Currently, for an uncomplicated MI, the patient might be discharged in 3-5 days. Although i.v. ribose may be more beneficial, if the patient has responded well and LV dysfunction is minimal, switching to an oral dose would be

TABLE 1

| Echo Indices | Treatment | Pre-MI | 2 wks post MI | 4 wks post MI |
| --- | --- | --- | --- | --- |
| LV diastolic diameter | Ribose | 0.64 ± 0.04 | 0.72 ± 0.08 | 0.76 ± 0.07* |
| (cm) | Control | 0.68 ± 0.03 | 0.79 ± 0.11 | 0.94 ± 0.07 |
| LV systolic diameter | Ribose | 0.39 ± 0.06 | 0.47 ± 0.22* | 0.64 ± 0.09* |
| (cm) | Control | 0.40 ± 0.03 | 0.73 ± 0.10 | 0.95 ± 0.07 |
| Septal diastolic | Ribose | 0.13 ± 0.02 | | 0.12 ± 0.02 |
| thickness (cm) | Control | 0.12 ± 0.01 | | 0.10 ± 0.01 |
| Posterior wall diastolic | Ribose | 0.13 ± 0.02 | 0.18 ± 0.12 | 0.13 ± 0.03* |
| thickness (cm) | Control | 0.13 ± 0.03 | 0.10 ± 0.01 | 0.10 ± 0.01 |
| Ejection fraction | Ribose | 76.4 ± 5.9 | 50.5 ± 5.9* | 49.1 ± 9.4* |
| (EF) % | Control | 76.3 ± 2.3 | 23.5 ± 12.6 | 31.2 ± 4.8 |
| Shortening fraction | Ribose | 38.6 ± 5.3 | 19.8 ± 4.4 | 19.9 ± 6.1* |
| (SF) % | Control | 38.9 ± 2.1 | 8.7 ± 5.3 | 10.7 ± 1.1 |

*$P < 0.05$ vs. control.

These data show that raising myocardial energy levels clearly improves function and, on the basis of known pathophysiology, is therefore expected to delay chronic changes, including apoptosis, in MI induced CHF conditions. Importantly, when administered for a prolonged period after the MI, ribose treatment reduces the progressive dilation and wall-thinning, characteristic of CHF, which untreated animals undergo. Critical systolic function (contractility) was also better preserved by long term ribose treatment. With improved ejection fraction (EF) and increased cardiac output, perfusion of the RM will be better maintained as will much of the border zone. The slide into failure would be expected to be reduced or even prevented.

In addition, reduced dilation of the LV was achieved with long term treatment. Because dilation is the hallmark of the progression to heart failure, the ability to reduce dilation is an important finding. In a similar vein, the LV wall thickness was much better preserved by long term ribose administration. The effect continued for the 2 weeks of i.v. ribose treatment, considered. On the other hand, if significant LV dysfunction still exists, the more effective, but more cumbersome, home i.v. ribose infusion might be chosen. The duration of oral pentose would also depend on LV function on follow-up echocardiograms. In some embodiments the oral pentose is continued for about 3-6 weeks initially with consideration to continue treatment for 3-6 months or even longer depending on status of ventricular function.

The patient is evaluated non-invasively to determine the efficacy of treatment and its duration. For example, the patient may be examined by echocardiogram frequently initially and later at weekly intervals following the MI. The echocardiogram will be used to provide evidence that the detrimental changes that signal CHF development (LV dilation and wall-thinning) have first stabilized then improved as well as to demonstrate systolic (e.g. EF, SF, LESV) and diastolic (e.g. LEDV, mitral and left atrial indices) functions have returned essentially to pre-MI levels. If these parameters show deterioration, particularly if there is no evidence for a new MI, then a period of more intensive therapy, including i.v. ribose, may be again undertaken.

All publications, patents and patent applications cited herein are hereby incorporated by reference as if set forth in their entirety herein. While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

I claim:

1. A method of limiting consequences of myocardial stress on cardiac energy levels in a patient diagnosed with myocardial stress and thereby limiting damage to normal cardiac tissue that begins a progression to chronic heart failure comprising providing to the patient a prolonged and continuous administration of a sufficient quantity of at least one ribose moiety that is a rate-limiting precursor to the synthesis of ATP, wherein the administration is initiated by parenteral administration of the at least one ribose moiety for an initial period of about 3 to about 14 days followed by oral administration of the at least one ribose moiety for at least 3 weeks, wherein the prolonged administration at least one ribose moiety is sufficient to normalize and maintain levels of ATP in the stressed myocardium.

2. The method of claim 1, wherein the ribose moiety is selected from one or more of ribose, D-ribose, ribulose, xylitol, xylulose, and a 5-carbon precursor of ribose.

3. The method of claim 1, wherein the myocardial stress immediately follows a myocardial infarction (MI).

4. The method of claim 1, wherein the myocardial stress is a result of one or more of: hypertension, cardiomyopathy, myocarditis, valvular regurgitation, severe lung disease, and severe anemia of chronic disease.

5. The method of claim 1, wherein the ribose moiety is a ribose or D-ribose and the prolonged and continuous administration is initiated by an acute loading dose equivalent to approximately 1 ml/kg of a 5% solution given over about 1-2 hours, followed by a subacute dose having a dosage equivalent of approximately 0.2 to about 0.4 ml/kg/hr of a 5% solution administered to the patient for at least 3 days thereafter.

6. The method of claim 1, wherein the oral administration is at a daily dose of 10-20 gms of the ribose moiety.

7. A method of limiting effects of stress placed on remaining, often normal, myocardium in patients at risk for developing chronic heart failure (CHF) and thereby limiting a progressive dysfunction that leads to (CHF), comprising: identifying a condition placing the patient at risk for development of CHF; immediately initiating continuous intravenous administration of a composition including a sufficient quantity of at least one ribose moiety into the patient; continuing the intravenous administration for at least three days up to a duration of a hospitalization of the patient; continuing administration of the at least one ribose moiety by oral dosage for at least three weeks following the intravenous administration while assessing one or more of LV, systolic, and diastolic function periodically during the oral administration of the at least one ribose moiety, and continuing the oral administration until one or more of the LV, systolic or diastolic function improves in the patient; and resuming intravenous administration of the at least one ribose moiety if one or more of the LV, systolic, and diastolic function declines.

8. The method of claim 7, wherein the ribose moiety is selected from one or more of ribose, D-ribose, ribulose, xylitol, xylulose, and a 5-carbon precursor of ribose.

9. The method of claim 7, wherein the condition placing the patient at risk for development of CHF is one or more of: myocardial infarction (MI), coronary artery disease, hypertension, cardiomyopathy, myocarditis, valvar regurgitation, severe lung disease, and severe anemia of chronic disease.

10. The method of claim 7, wherein the condition placing the patient at risk for development of CHF is a period of an acute injurious episode immediately following a myocardial infarction (MI).

11. The method according to claim 5 wherein at least one of the acute loading dose and the subacute dose further comprises a glucose solution.

* * * * *